US009198674B2

(12) United States Patent
Benson et al.

(10) Patent No.: US 9,198,674 B2

(45) Date of Patent: Dec. 1, 2015

(54) SURGICAL INSTRUMENT AND METHOD

(71) Applicant: Warsaw Orthopedic, Inc., Warsaw, IN (US)

(72) Inventors: Nicholas M. Benson, Cordova, TN (US); Steven D. DeRidder, Bartlett, TN (US)

( * ) Notice: Subject to any disclaimer, the term of this patent is extended or adjusted under 35 U.S.C. 154(b) by 365 days.

(21) Appl. No.: 13/715,494

(22) Filed: Dec. 14, 2012

(65) Prior Publication Data

US 2014/0171946 A1 Jun. 19, 2014

(51) Int. Cl.

*A61B 17/16* (2006.01)
*A61B 17/17* (2006.01)
*A61B 17/34* (2006.01)
*A61B 17/32* (2006.01)

(52) U.S. Cl.

CPC ............. *A61B 17/1655* (2013.01); *A61B 17/17* (2013.01); *A61B 17/34* (2013.01); *A61B 17/3417* (2013.01); *A61B 17/3421* (2013.01); *A61B 17/3468* (2013.01); *A61B 2017/320052* (2013.01); *A61B 2017/347* (2013.01); *A61B 2017/3445* (2013.01); *A61B 2017/3447* (2013.01)

(58) Field of Classification Search

CPC ............... A61B 17/1655; A61B 17/17; A61B 2017/320052; A61B 17/34; A61B 17/3417; A61B 17/3421; A61B 2017/3445; A61B 2017/3447; A61B 17/3468; A61B 2017/347

See application file for complete search history.

(56) References Cited

U.S. PATENT DOCUMENTS

| | | | | |
|---|---|---|---|---|
| 5,242,427 | A * | 9/1993 | Bilweis | 604/264 |
| 6,951,562 | B2 * | 10/2005 | Zwirnmann | 606/80 |
| 7,465,304 | B1 * | 12/2008 | Haufe et al. | 606/79 |
| 2005/0256525 | A1 * | 11/2005 | Culbert et al. | 606/53 |
| 2010/0145142 | A1 * | 6/2010 | Begemann et al. | 600/104 |
| 2011/0251597 | A1 * | 10/2011 | Bharadwaj et al. | 606/1 |

* cited by examiner

*Primary Examiner* — Larry E Waggle, Jr.

(57) ABSTRACT

A surgical instrument comprises a first member including an inner surface defining a passageway and a lock. A second member is disposable within the first passageway. The second member comprises an inner surface defining a passageway and extending between a first end comprising a lock and a second end configured to engage tissue. A third member is disposable within the second passageway. The third member extends between a first end and a second end configured to penetrate tissue and form a cavity therein. The first lock is engageable with the second member to prevent relative movement of the second member and the second lock is engageable with the third member to prevent relative movement of the third member. Systems and methods are disclosed.

19 Claims, 13 Drawing Sheets

SURGICAL INSTRUMENT AND METHOD

TECHNICAL FIELD

The present disclosure generally relates to medical devices for the treatment of musculoskeletal disorders, and more particularly to a surgical system for creating a surgical pathway and/or preparing a surgical site, and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, implants such as bone fasteners, connectors, plates and vertebral rods are often used to provide stability to a treated region. These implants can redirect stresses away from a damaged or defective region while healing takes place to restore proper alignment and generally support the vertebral members. Surgical instruments, such as, for example, wires and cannulated instrumentation can be employed to establish passageways for delivery of the implants. This disclosure describes an improvement over these prior art technologies.

SUMMARY

In one embodiment, in accordance with the principles of the present disclosure, a surgical instrument is provided. The surgical instrument comprises a first member including an inner surface defining a first passageway and a first lock. A second member is disposable within the first passageway and movable relative to the first member. The second member comprises an inner surface defining a second passageway and extending between a first end comprising a second lock and a second end configured to engage tissue. A third member is disposable within the second passageway and movable relative to the second member. The third member extends between a first end and a second end configured to penetrate tissue and form a cavity therein. The first lock is engageable with the second member to prevent relative movement of the second member and the second lock is engageable with the third member to prevent relative movement of the third member.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
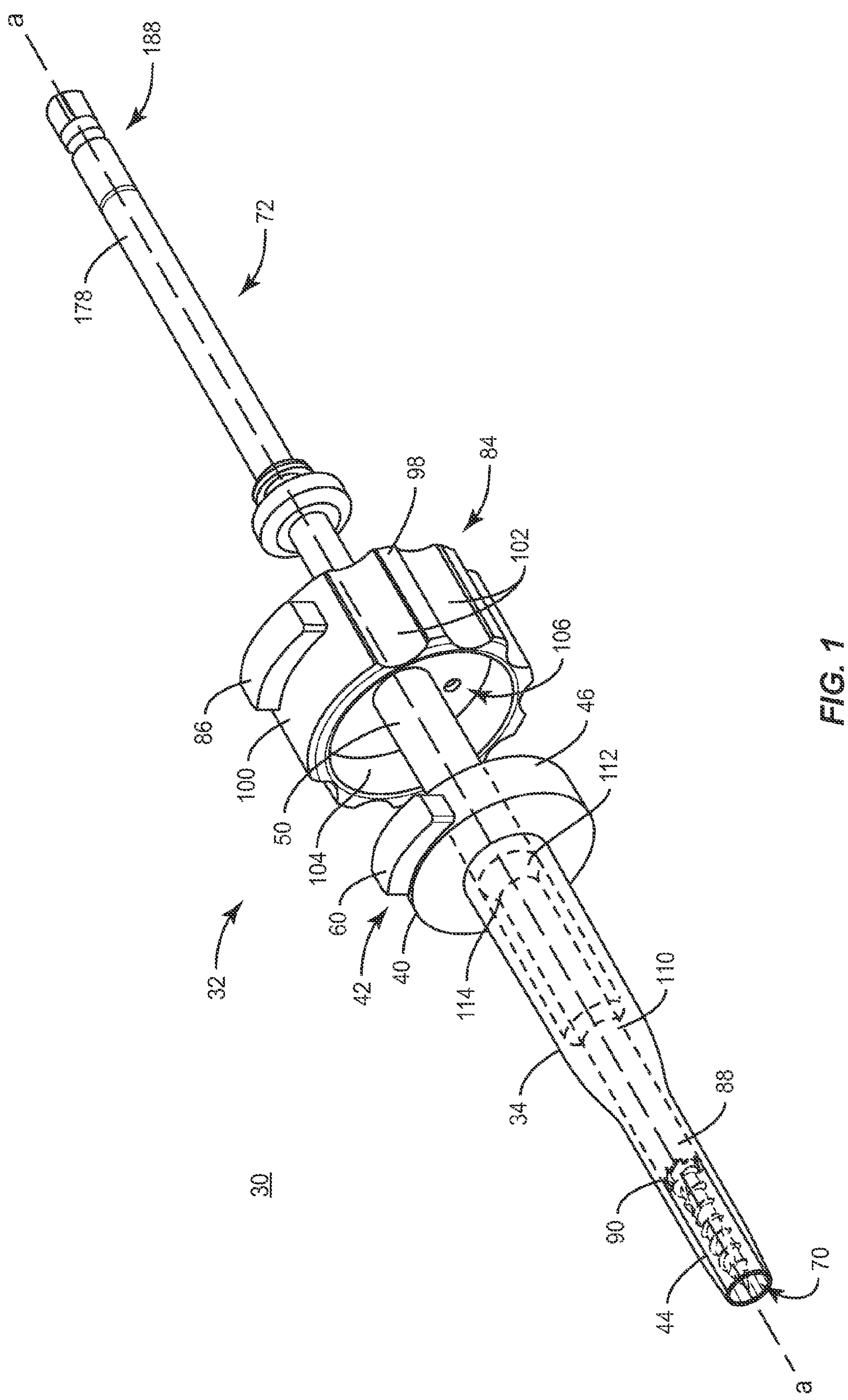
FIG. 1 is a perspective view of one particular embodiment of a surgical instrument in accordance with the principles of the present disclosure, in part phantom.

The exemplary embodiments of a surgical system are discussed in terms of medical devices for the treatment of musculoskeletal disorders and more particularly, in terms of a surgical implant system for creating a surgical pathway and/or preparing a surgical site, and a method for treating a spine.

In one embodiment, the system includes a surgical instrument that includes a tap, such as, for example, a screw tap for fixing an implant, such as, for example, a screw, into a portion of the anatomy of a patient, such as, for example, the spine. The disclosed surgical instrument facilitates placement of implants by avoiding use of complicated and costly instrumentation, in an effort to shorten the duration of surgery.

In one embodiment, the system includes a tap sleeve that allows a medical practitioner to percutaneously navigate through an incision in a patient to and from a desired location within the anatomy of the patient, such as, for example, the spine to avoid undesired tearing of soft tissue. The tap sleeve includes an inner toothed sleeve positioned within an outer protective sleeve. This dual sleeve configuration facilitates percutaneous docking of the inner toothed sleeve for positive docking with tissue, such as, for example, cortical bone, while the outer protective sleeve houses the inner toothed sleeve during delivery of the tap sleeve to the desired location within the anatomy of the patient.

In one embodiment, the tap sleeve includes a tap, such as, for example, a bone tap, positioned within the inner toothed sleeve configured to penetrate tissue, such as, for example, bone. In one embodiment, the tap sleeve includes safety features that prevent deployment of the inner toothed sleeve and/or the bone tap from the outer protective sleeve until the outer protective sleeve has navigated to a desired location within the anatomy of patient to resist or prevent inadvertent or accidental exposure of the sharp bone tap and/or toothed sleeve during navigation to and from the desired location. In one embodiment, once the toothed sleeve is deployed and docked, tapping of the bone may begin.

In one embodiment, at least one of the components of the bone tap, such as, for example, the outer protective sleeve, is made from a radiolucent material to facilitate visualization of the tap sleeve for accurate and selective placement during navigation to a desired location without the risk of the sharp bone tap and/or the inner toothed sleeve undesirably damaging soft tissue.

In one embodiment, the system includes a surgical instrument having two fenestrated members where one member is directed by the other for temporarily docking or fixing to an animal subject. In one embodiment, the system includes an assembly having two or more fenestrated extensions where one of the extensions has a targeted receiving area for another extension. In one embodiment, the system includes an assembly having two or more fenestrated extensions wherein one of the extensions moves freely from the other extensions and one of the extensions has the ability to actively dock in an animal subject. In one embodiment, the system includes two or more devices where one of the devices serves as a guide and one or more of the devices have temporary or safety locking or restraining features for at least one of the other devices. In one embodiment, the system includes one or more cannulated extenders configured to fit within one another so as to function together and connect to an animal subject for purposes of directing an implant, such as, for example, a bone anchor.

It is envisioned that the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the system of the present disclosure may be employed with other osteal and bone related applications, including those associated with diagnostics and therapeutics. It is further contemplated that the disclosed system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-13, there is illustrated components of a surgical implant system 30 including a surgical instrument 32, in accordance with the principles of the present disclosure.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 30 may have material composites, including the above materials, to achieve various desired characteristics such as strength, rigidity, elasticity, compliance, biomechanical performance, durability and radiolucency or imaging preference. The components of system 30, individually or collectively, may also be fabricated from a heterogeneous material such as a combination of two or more of the above-described materials. The components of system 30 may be monolithically formed, integrally connected or include fastening elements and/or instruments, as described herein.

System 30 is employed, for example, with an open or mini-open, minimal access and/or minimally invasive including percutaneous surgical technique to create a cavity for an implant, such as, for example, a bone fastener at a surgical site within a body of a patient, for example, a section of a spine. In one embodiment, the components of system 30 are configured to create a threaded cavity to fix a spinal rod, connector and/or plate to a spine via a bone fastener for a surgical treatment to treat various spine pathologies, such as those described herein.

Figure 3:
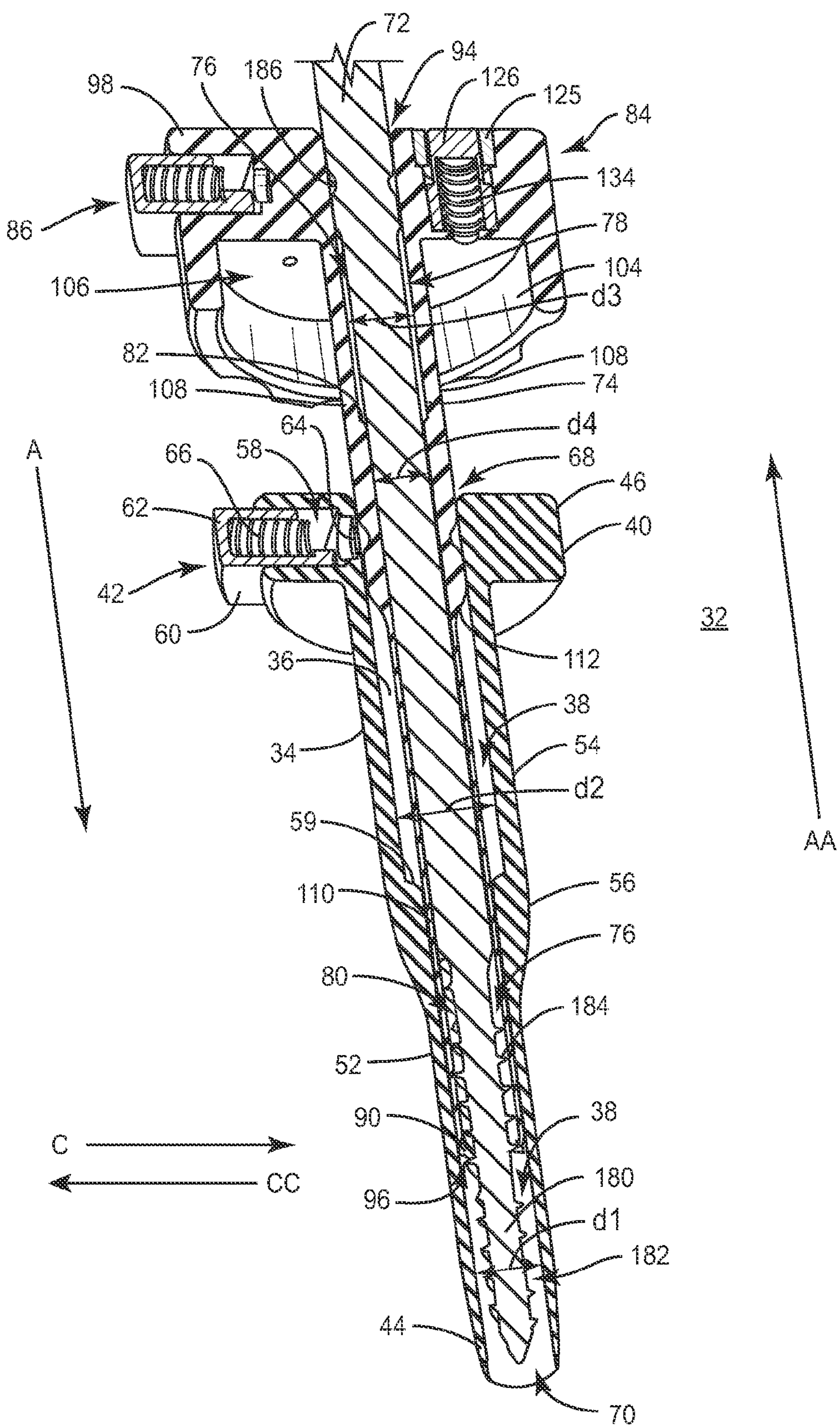
FIG. 3 is a perspective view of the instrument shown in FIG. 1 shown in cross-section.

Instrument 32 includes a first member, such as, for example, an outer protective sleeve 34 defining a longitudinal axis a and including an inner surface 36 defining a passageway 38, as shown in FIG. 3. Sleeve 34 extends between a first end 40 comprising a first transverse lock 42 biased to a locking orientation and a second end 44 configured for disposal adjacent a surgical site. Sleeve 34 has an outer surface that is smooth or even to prevent injury to the anatomy of a patient, such as, for example, soft tissue, when instrument 32 is inserted through an incision and delivered to the surgical site. It is contemplated that all or only a portion of the outer surface of sleeve 32 may have various surface configurations, such as, for example, rough, threaded, arcuate, undulating, porous, semi-porous, dimpled, polished and/or textured, to enhance fixation of instrument 32 with tissue.

Figure 2:
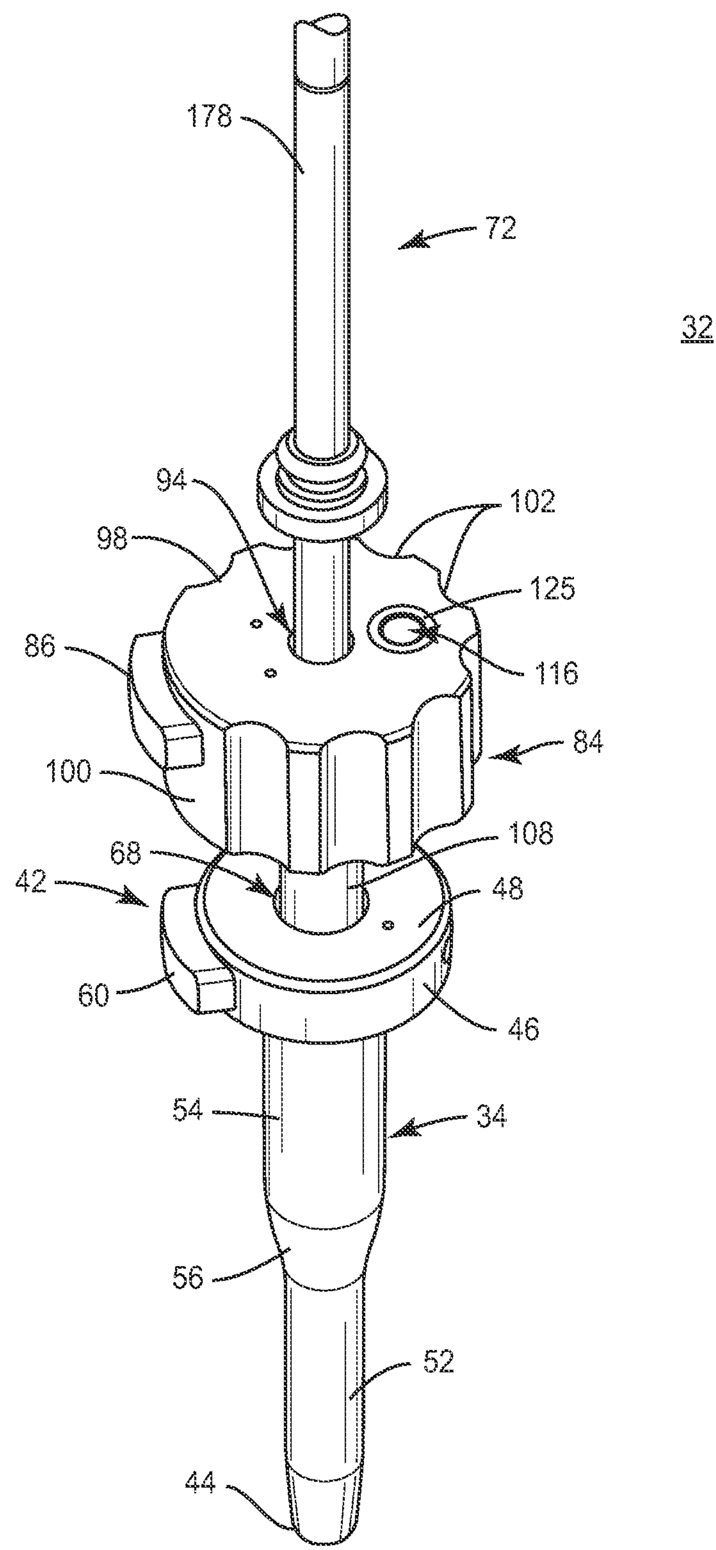
FIG. 2 is a perspective view of the instrument shown in FIG. 1.

End 40 includes a disc portion 46 having an outer surface 48 having a first diameter configured to engage an inner surface of a second member, such as, for example, an inner sleeve 50, as shown in FIG. 1. Sleeve 34 includes a first section 52 adjacent end 44 having an outer surface with a second diameter that is less than the first diameter. Sleeve 34 includes a second section 54, as shown in FIG. 2, positioned between portion 46 and section 52 having an outer surface with a third diameter that is less than the first diameter, and greater than the second diameter. Sleeve 34 includes a tapered section 56 between sections 52, 54. Portion 46 and sections 52, 54 each have a circular cross sectional configuration. It is envisioned that portion 46, section 52 and/or section 54 may have alternate cross section configurations, such as, for example, oval, oblong, triangular, square, hexagonal, polygonal, irregular, uniform, non-uniform and/or tapered.

Passageway 38 has a uniform diameter d1 through sections 52, 56 and a uniform diameter d2 through section 54 that is greater than diameter d1, as shown in FIG. 3. Passageway 38 has a circular cross sectional configuration through sections 52, 56 and through section 54. It is envisioned that the portion of passageway 38 that extends through sections 52, 56 and/or the portion of passageway 38 that extends through section 54 may have alternate cross section configurations, such as, for example, oval, oblong, triangular, square, hexagonal, polygonal, irregular, uniform, non-uniform and/or tapered.

In one embodiment, surface 36 defines a circumferential flange 59 within passageway 38 between section 54 and section 56, as shown in FIG. 3. Flange 59 is configured to engage a portion of sleeve 50 to prevent sleeve 50 from moving beyond flange 59 within passageway 38, in the direction shown by arrow A. Flange 59 extends at an acute angle relative to axis a. It is envisioned that flange 59 may be disposed at alternate orientations, relative to axis a, such as, for example, transverse, perpendicular and/or other angular orientations such as or obtuse, according to the requirements of a particular application.

Lock 42 includes a channel 58 extending transverse to axis a into section 46 through surface 40 without extending through surface 36, as shown in FIG. 3. A tab 60 is positioned in channel 58. Channel 58 has a rectangular cross sectional configuration. In one embodiment, channel 58 includes a recess 64 extending into portion 46 having a diameter that is less than a diameter of channel 58. Recess 64 includes a spring 66 disposed therein. A first end of spring 66 is disposed in recess 64 and an opposite second end of spring 66 engages an inner surface of tab 60 such that tab 60 is spring-loaded within channel 58. This configuration allows lock 42 to be resiliently biased to a locking orientation such that tab 60 protrudes from portion 46.

Sleeve 34 includes a first opening 68 in communication with passageway 38 at end 40 configured for moveable disposal of sleeve 50, as shown in FIG. 3. Sleeve 34 further includes a second opening 70 in communication with passageway 38 at end 44 configured for passage of sleeve 50 and/or a third member, such as, for example, a tap 72. Openings 68, 70 each have circular cross sectional configurations. It is envisioned that opening 68 and/or opening 70 may have alternate cross section configurations, such as, for example, oval, oblong, triangular, square, hexagonal, polygonal, irregular, uniform, non-uniform and/or tapered.

Sleeve 50 is movably disposable within passageway 38 and includes an inner surface 74 defining a passageway 76, as shown in FIG. 3. Passageway 76 includes a first segment 78 having a diameter d3 and a second segment 80 distal of segment 78 having a diameter d4. Diameter d4 is less than diameter d3 and diameter d4 is less than diameter d1. Diameter d3 is substantially equivalent to diameter d1.

In one embodiment, surface 74 defines a circumferential flange 82 within passageway 76 between segments 78, 80 configured to engage a portion of tap 72 to prevent tap 72 from moving beyond flange 82 within passageway 76 in the direction shown by arrow A. Flange 82 extends at an acute angle relative to axis a. It is envisioned that flange 82 may be disposed at alternate orientations, relative to axis a, such as, for example, transverse, perpendicular and/or other angular orientations such as obtuse, according to the requirements of a particular application.

Figure 5:
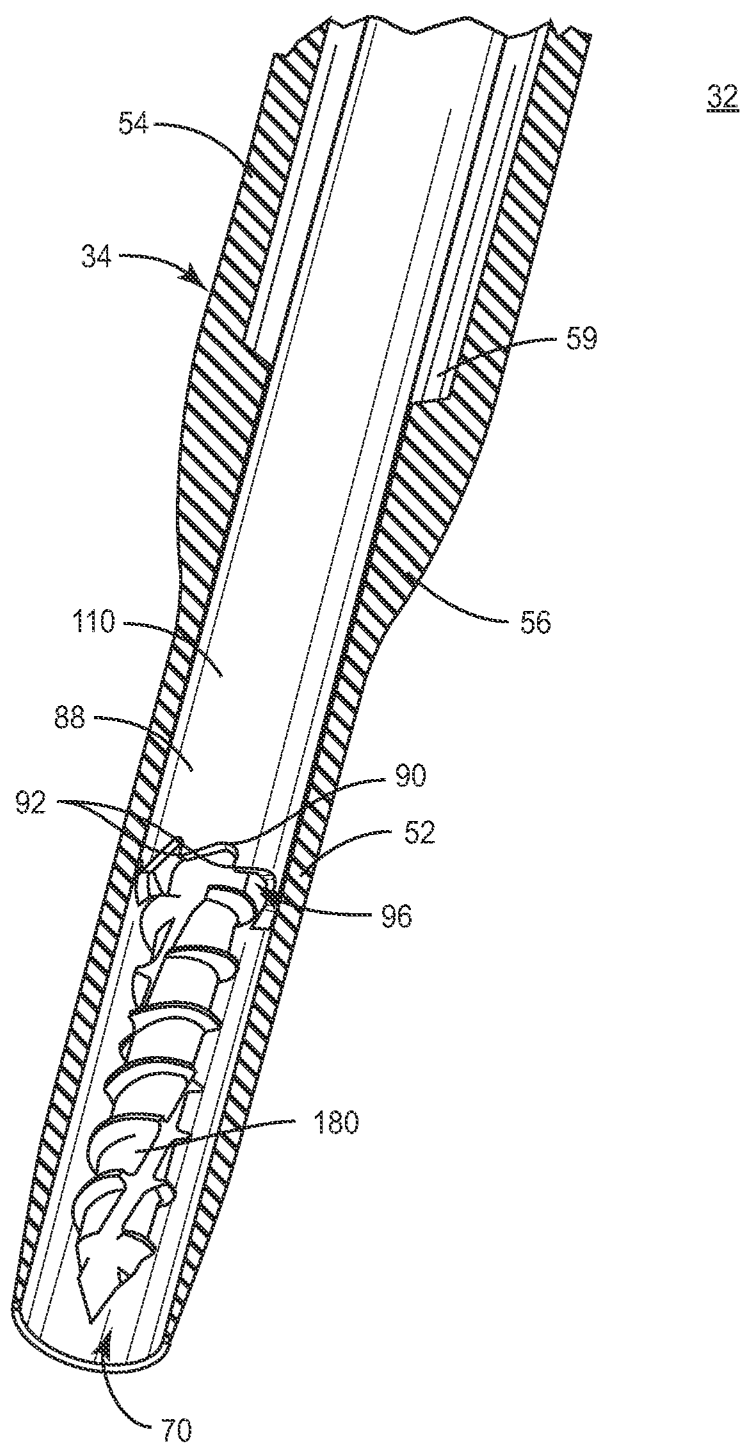
FIG. 5 is an enlarged, break away perspective view of the instrument shown in FIG. 1, in part phantom.

Sleeve 50 extends between a first end 84 comprising a second transverse lock 86 and a second end 88 configured to engage tissue. End 88 includes a distal face 90 having at least one penetrating element engageable with tissue, such as, for example, a plurality of teeth 92, as shown in FIG. 5. Sleeve 50 includes a first opening 94 in communication with passageway 76 at end 84 configured for disposal of tap 72, as shown in FIG. 3. Sleeve 50 further includes a second opening 96 in communication with passageway 76 at end 88 configured for passage of tap 72. Openings 94, 96 each have circular cross sectional configurations. It is envisioned that opening 94 and/or opening 96 may have alternate cross section configurations, such as, for example, oval, oblong, triangular, square, hexagonal, polygonal, irregular, uniform, non-uniform and/or tapered.

End 84 includes a handle portion 98 having an outer surface 100 that includes a plurality of spaced apart concave grooves 102, as shown in FIG. 1, configured for gripping by a medical practitioner. Grooves 102 each extend parallel to axis a and include convexly curved projections therebetween. It is envisioned that grooves 102 may be disposed at alternate orientations, relative to axis a, such as, for example, transverse, perpendicular and/or other angular orientations such as acute or obtuse, according to the requirements of a particular application. It is contemplated that all or only a portion of the surface 100 may have various surface configurations, such as, for example, rough, arcuate, undulating, porous, semi-porous, dimpled, polished and/or textured, to facilitate gripping by a medical practitioner. It is further contemplated that grooves 102 and/or the projections between grooves 102 may be variously configured and dimensioned, such as, for example, planar, concave, convex, polygonal, irregular, uniform, non-uniform, staggered, tapered, consistent or variable, depending on the requirements of a particular application.

A distal end of portion 98 includes an inner surface 104 defining a recessed portion 106 configured to receive portion 46 such that surface 48 engages surface 104 to engage sleeve 34 with sleeve 50 and prevent axial translation of sleeve 50 relative to sleeve 34, in the direction shown by arrow A, and/or translation of sleeve 34 relative to sleeve 50, in the direction shown by arrow AA. When surface 48 engages surface 104, end 88 is disposed in a nested configuration within sleeve 34, as shown in FIGS. 6, 7 and 9-11, for example. Portion 106 has a depth that is less than a height of portion 46 such that only part of portion 46 is disposed within portion 106 when surface 48 is engaged with surface 104. It is contemplated that the depth of portion 106 is such that at least a portion of an outer surface of tab 60 engages surface 104 when end 88 is disposed in the nested configuration within sleeve 34. It is envisioned that the outer surface of tab 60 engages surface 104 when end 88 is disposed in the nested configuration within sleeve 34. In one embodiment, the depth of portion 106 is equal to or greater than the height of portion 46 such that portion 46 is completely disposed within portion 106 when surface 48 is engaged with surface 104. It is envisioned that surface 104 may include one or more cavities configured to receive at least a portion tab 60 when end 88 is disposed in the nested configuration within sleeve 34.

Sleeve 50 includes a proximal section 108 adjacent portion 98 and a distal section 110 adjacent section 108 and spaced apart from portion 98, as shown in FIG. 3. Sections 108, 110 each have a diameter that is less than a diameter of portion 98. Sections 108, 110 are each substantially cylindrical and include a circular cross sectional configuration. Section 108 has a diameter that is greater than a diameter of section 110. Sleeve 50 includes a tapered intermediate section 112 positioned between sections 108, 110. It is envisioned that section 108, section 110 and/or section 112 may have alternate cross section configurations, such as, for example, oval, oblong, triangular, square, hexagonal, polygonal, irregular, uniform, non-uniform and/or tapered. In one embodiment, section 112 defines an engaging surface 114 configured to engage flange 59 when sleeve 50 is positioned within sleeve 34 to prevent sleeve 50 from translating axially within passageway 38, in the direction shown by arrow A.

Figure 10:
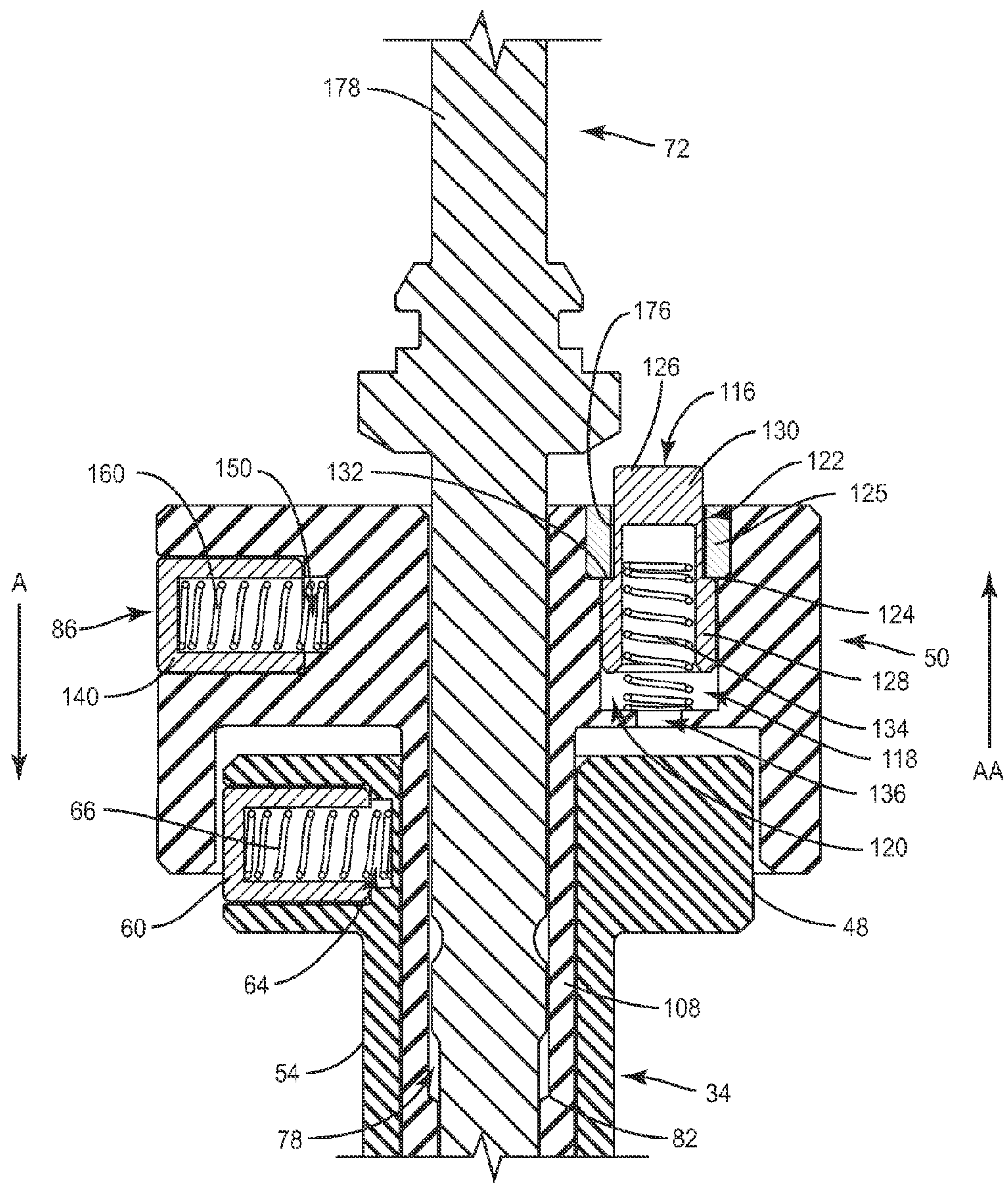
FIG. 10 is a side view of a portion of the instrument shown in FIG. 9 shown in cross-section.

Sleeve 50 includes a third lock 116 extending parallel to axis a through surface 100 configured to engage lock 86 to fix lock 86 in a locking orientation to prevent relative movement of tap 72. Lock 116 includes a channel 118 extending parallel to axis a into portion 98 through surface 100 without extending through surface 104, as shown in FIG. 10. Channel 118 includes a first section 120 and a second section 122 having a diameter that is greater than a diameter of section 120. A collar 125 is positioned within section 122 and engages a ledge between sections 120, 122. Collar 125 defines an interface 124 configured to engage the ledge between sections 120, 122 and a tab 126 of lock 116 to prevent tab 126 from translating axially, in the direction shown by arrow AA beyond interface 124. Sections 120, 122 each have a circular cross sectional configuration. Collar 125 has a diameter that is greater than a diameter of section 120 to prevent collar 125 from translating axially, in the direction shown by arrow A, beyond interface 124. It is envisioned that section 120 and/or section 122 may have alternate cross section configurations, such as, for example, oval, oblong, triangular, square, hexagonal, polygonal, irregular, uniform, non-uniform and/or tapered. It is further envisioned that lock 116 and/or channel 118 may be disposed at alternate orientations, relative to axis a, such as, for example, transverse, perpendicular and/or other angular orientations such as acute or obtuse, coaxial and/or may be offset or staggered, according to the requirements of a particular application.

Tab 126 is positioned in channel 118. Tab 126 includes a first part 128 configured for disposal in section 120 and a proximal second part 130 configured for disposal in section 122. Tab 126 further includes a ledge 132 extending transverse to axis a positioned between parts 128, 130 configured to engage interface 124 to prevent tab 126 from translating axially within channel 118 beyond interface 124, in the direction shown by arrow A. Channel 118 includes a spring 134 disposed therein. A first end of spring 134 engages a bottom surface of channel 118 while an opposite second end of spring 134 engages an inner surface of tab 126 such that tab 126 is spring-loaded within channel 118. Part 128 has a height that is less than a depth of section 120 and part 130 has a height that is less than a depth of section 122. This configuration allows lock 116 to be resiliently biased to a non-locking orientation such that tab 126 protrudes from surface 100. In one embodiment, channel 118 includes a recess 136 extending into the bottom surface of channel 118 having a diameter that is less than a diameter of section 122. It is envisioned that the first end of spring 134 may be disposed in recess 136 and the second end of spring 134 engages the inner surface of tab 126. In one embodiment, an outer surface of part 130 includes a plurality of spaced apart grooves each extending parallel to axis a configured to engage protrusions on tab 140 to maintain lock 86 in a locking configuration.

Figure 12:
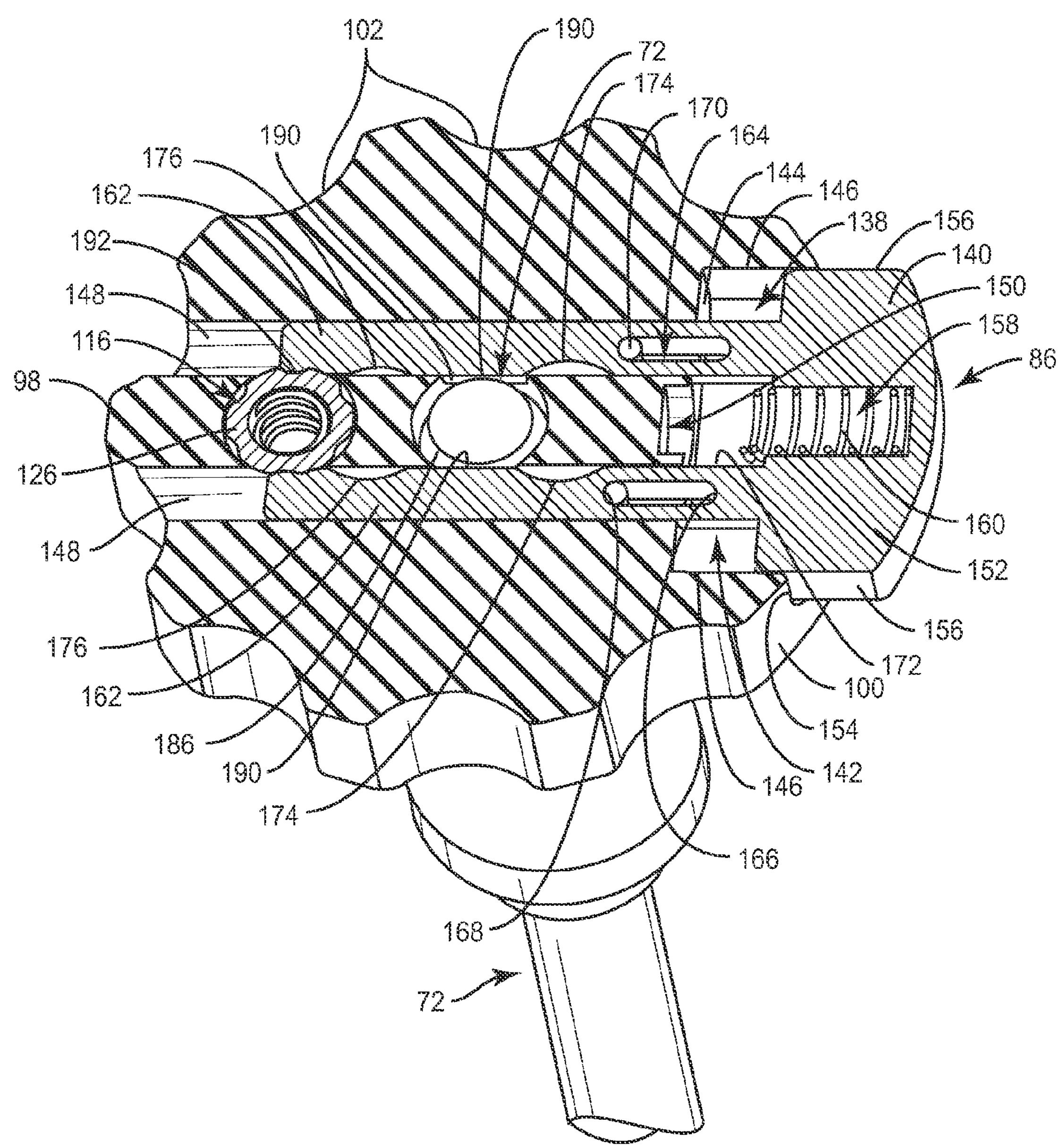
FIG. 12 is a perspective view of components of the instrument shown in FIG. 1 shown in cross-section.
Figure 13:
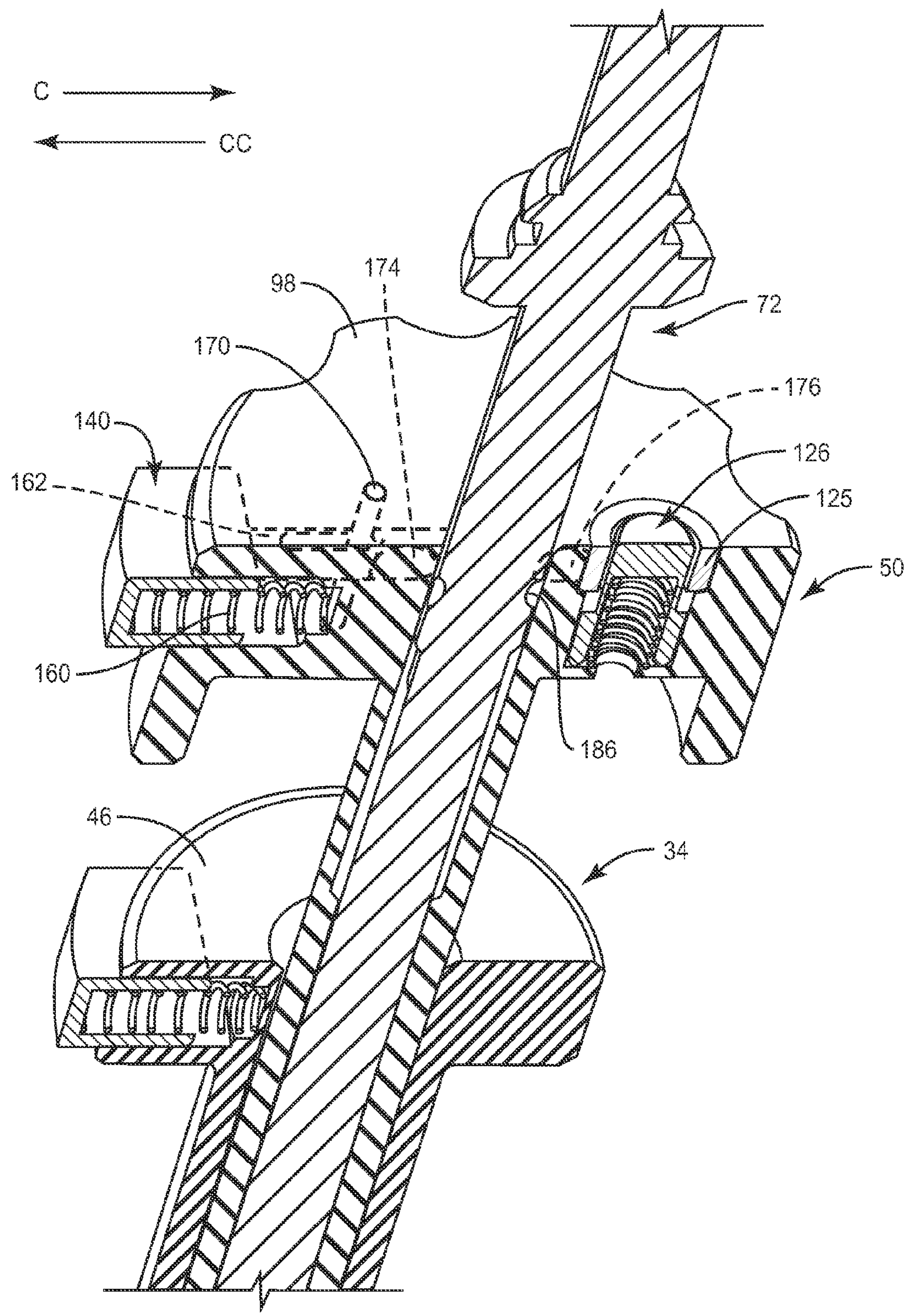
FIG. 13 is a perspective view of a portion of the instrument shown in FIG. 1 shown in cross-section, in part phantom.

Lock 86 includes a cavity 138 extending transverse to axis a into surface 100 configured for disposal of tab 140, as shown in FIG. 12. Cavity 138 includes a first section 142 defined by a transverse wall 144 extending between parallel sidewalls 146. Cavity 138 further includes a pair of spaced apart conduits 148 extending transverse to wall 144 through surface 100. Conduits 148 extend parallel to one another and are configured for moveable disposal of portions of tab 140. Cavity 138 includes a transverse recess 150 extending into wall 144 without extending through surface 100 configured for disposal of a portion of tab 140. Conduits 148 and recess 150 each have a uniform diameter and a cylindrical cross sectional configuration. It is envisioned that conduits 148 and/or recess 150 may have alternate cross section configurations, such as, for example, oval, oblong, triangular, square, hexagonal, polygonal, irregular, uniform, non-uniform and/or tapered.

Tab 140 includes a body 152 configured for moveable disposal in section 142. Body includes a transverse wall 154 extending between parallel sidewalls 156. When lock 86 is in a non-locking orientation, wall 144 engages wall 154 and sidewalls 146 engage sidewalls 156. An inner surface of body 152 defines a cavity 158 configured for disposal of a spring 160. A first end of spring 160 engages and end surface of recess 150 and a second end of spring 160 opposite the first end engages and end wall of cavity 158. This configuration allows lock 86 to be resiliently biased to a locking orientation such that tab 140 protrudes from surface 100 and relative movement of tap 72 is prevented.

Tab 140 includes a pair of spaced apart arms 162 extending transverse to wall 154 from body 152. Arms 162 are parallel to one another and are configured for moveable disposal in conduits 148. Arms 162 are distal to collar 125 and each extend from a first end adjacent wall 154 to a second end opposite the first end. Arms 162 each include an oblong opening 164 extending between a first end 166 and a second end 168. Openings 164 are each configured for disposal of a pin 170. Pins 170 extend parallel to axis a and are fixed in place within portion 98. It is envisioned that all or only a portion of each opening 164 may have alternate cross section configurations, such as, for example, circular, oval, triangular, square, polygonal, and/or tapered, depending upon the requirements of a particular application.

Arms 162 each include an inner surface 172. Surfaces 172 face one another and each include a first arcuate portion 174 positioned between opening 162 and the second end of arm 162 and a second arcuate portion 176 positioned between portion 174 and the second end of arm 162. Portions 174, 176 are concavely curved. Surfaces 172 are planar between wall 154 and portion 174, between portion 174 and portion 176, and between portion 176 and the second end of arm 162. Each surface 172 includes a planar locking section 190 between portion 174 and portion 176 configured for disposal in a groove 186 in tap 72 to prevent axial translation of tap 72 within passageway 76 in the direction show by arrow A and/or the direction shown by arrow AA. In one embodiment, the second ends of arms 162 each include a section 192 having a plurality of convexly curved projections between concavely curved gaps. The projections of sections 192 are configured for disposal in the grooves in tab 126 to fix lock 86 in a locking orientation. It is envisioned that portions 174, portions 176, sections 190 and/or sections 192 may be variously configured and dimensioned, such as, for example, planar, concave, convex, polygonal, irregular, uniform, non-uniform, staggered, tapered, consistent or variable, depending on the requirements of a particular application.

Figure 7:
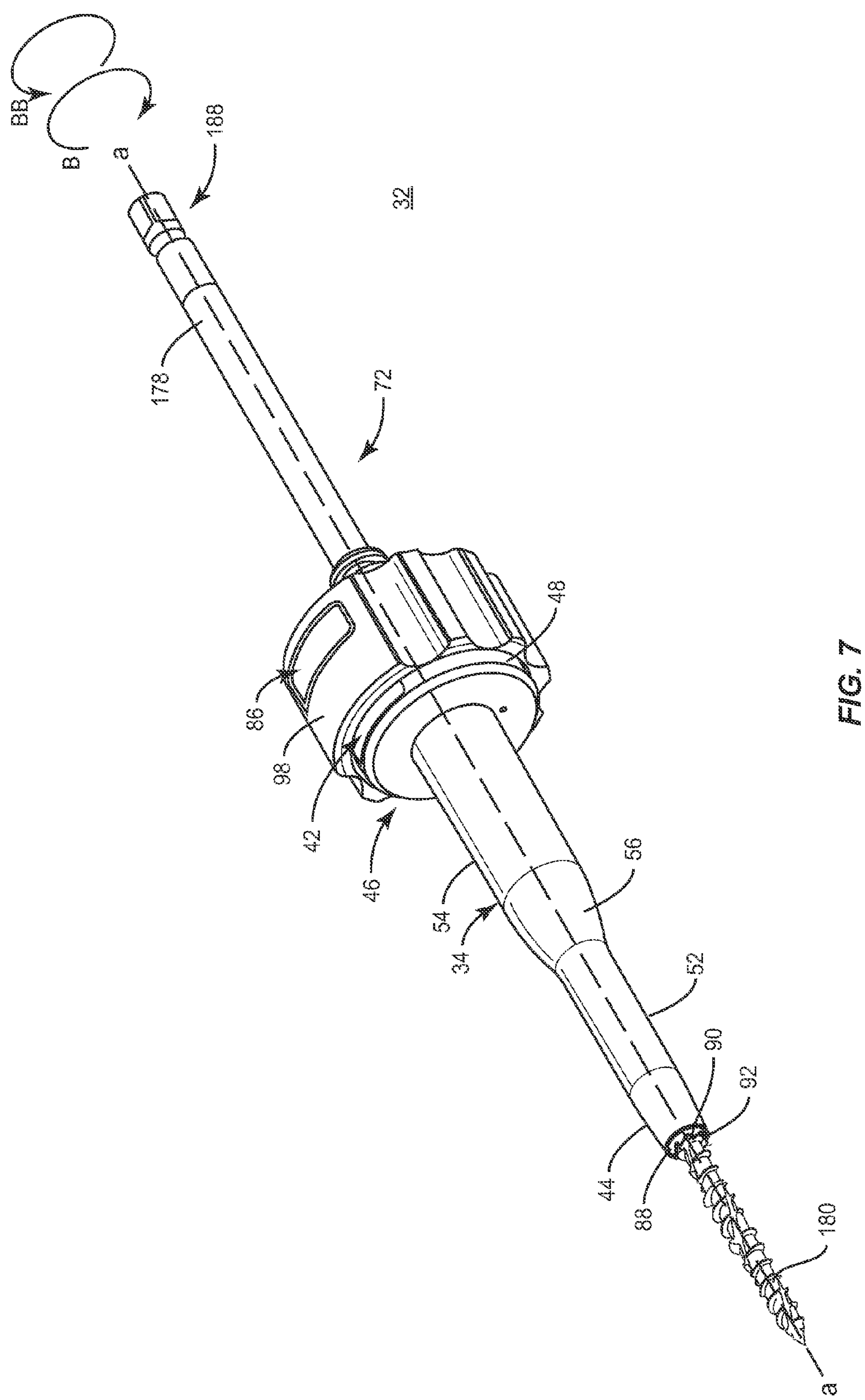
FIG. 7 is a perspective view of the instrument shown in FIG. 1.

Tap 72 is disposable within passageway 76 and is moveable relative to sleeve 50. Tap 72 extends between a first end 178, as shown in FIG. 7, and a second end 180 including a screw tap 182, as shown in FIG. 3, configured to penetrate tissue and form a cavity therein. Tap 182 includes an external or male thread 184 configured to form an internal or female thread in the tissue such that an implant, such as, for example, a bone fastener, can be threaded into the internal thread formed by tap 182.

Figure 4:
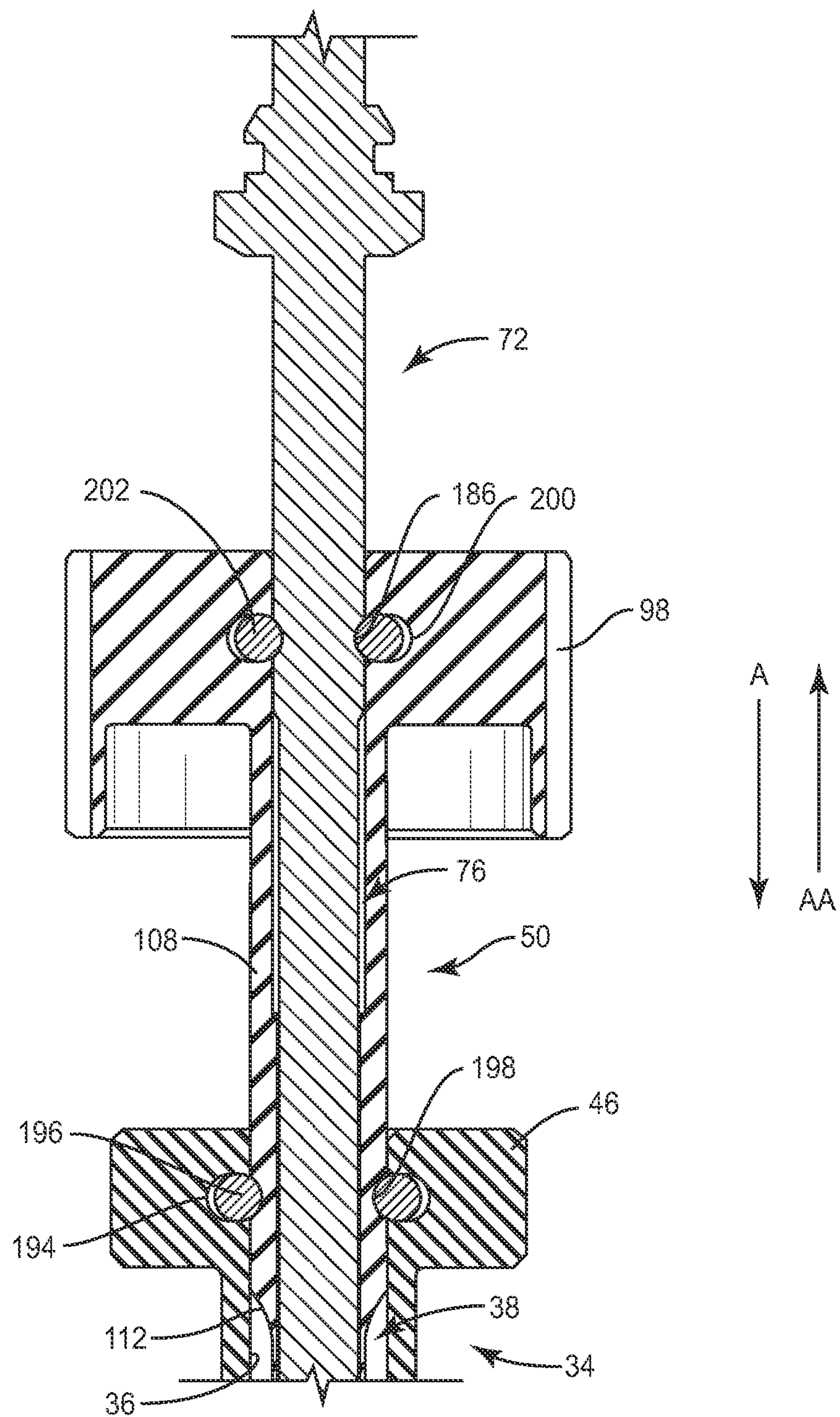
FIG. 4 is a top view of a portion of the instrument shown in FIG. 1 shown in cross-section.

Groove 186 extends transverse to axis a between ends 178, 180, as shown in FIG. 4. Groove 186 is configured for disposal with sections 190, as shown in FIG. 12, to prevent tap 72 from translating axially relative to sleeve 50, in the direction shown by arrow A or arrow AA. It is envisioned that groove 186 may be disposed at alternate orientations, relative to axis a, such as, for example, transverse, perpendicular and/or other angular orientations such as acute or obtuse, coaxial and/or may be offset or staggered, according to the requirements of a particular application. It is further envisioned that tap 72 may include one or a plurality of grooves 186 disposed at various locations along tap 72 to vary the position of tap 182 relative to end 44 and/or end 88. In one embodiment, tap 72 includes a first groove 186 configured to fix tap 72 in position relative to sleeve 50 such that tap 182 projects through opening 70 and/or opening 96 and a second groove 186 configured to fix tap 72 in position relative to sleeve 50 such that tap 182 is positioned within passageway 38 and/or passageway 76 without extending through opening 70.

End 178 includes a drive portion 188, as shown in FIG. 1, configured to rotate tap 72, in the direction shown by arrow B and/or the direction shown by arrow BB. It is envisioned that portion 188 may be configured to engage an actuator, such as, for example, a surgical instrument, powered drill, hand drill, driver or other tool to rotate tap 72, in the direction shown by arrow B and/or the direction shown by arrow BB. In one embodiment, portion 188 has a hexagonal cross sectional configuration and is configured to engage a correspondingly shaped portion of the actuator. It is envisioned that portion 188 may include a square, triangular, polygonal, star or hexalobe cross sectional configuration configured engage a correspondingly shaped portion of the actuator.

Figure 8:
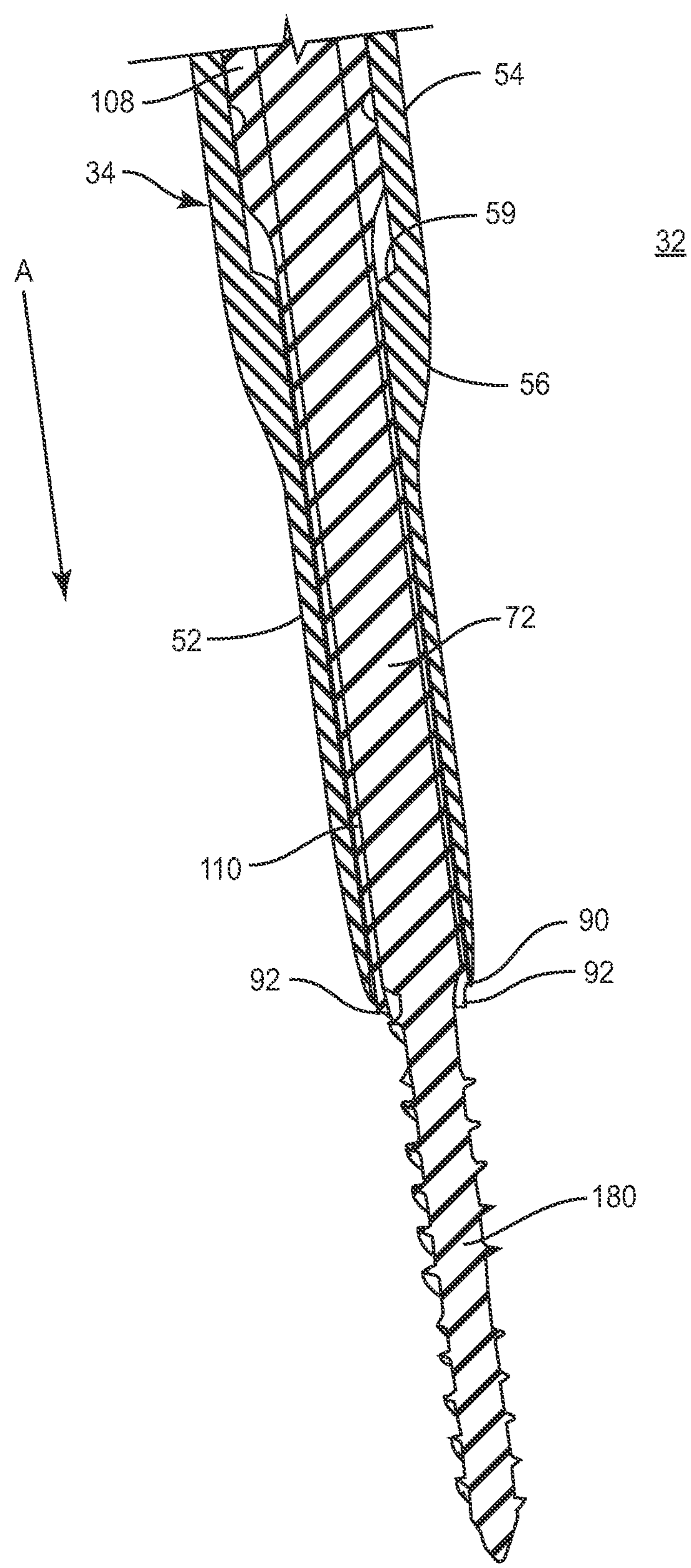
FIG. 8 is an enlarged, break away perspective view of the instrument shown in FIG. 7 shown in cross-section.
Figure 9:
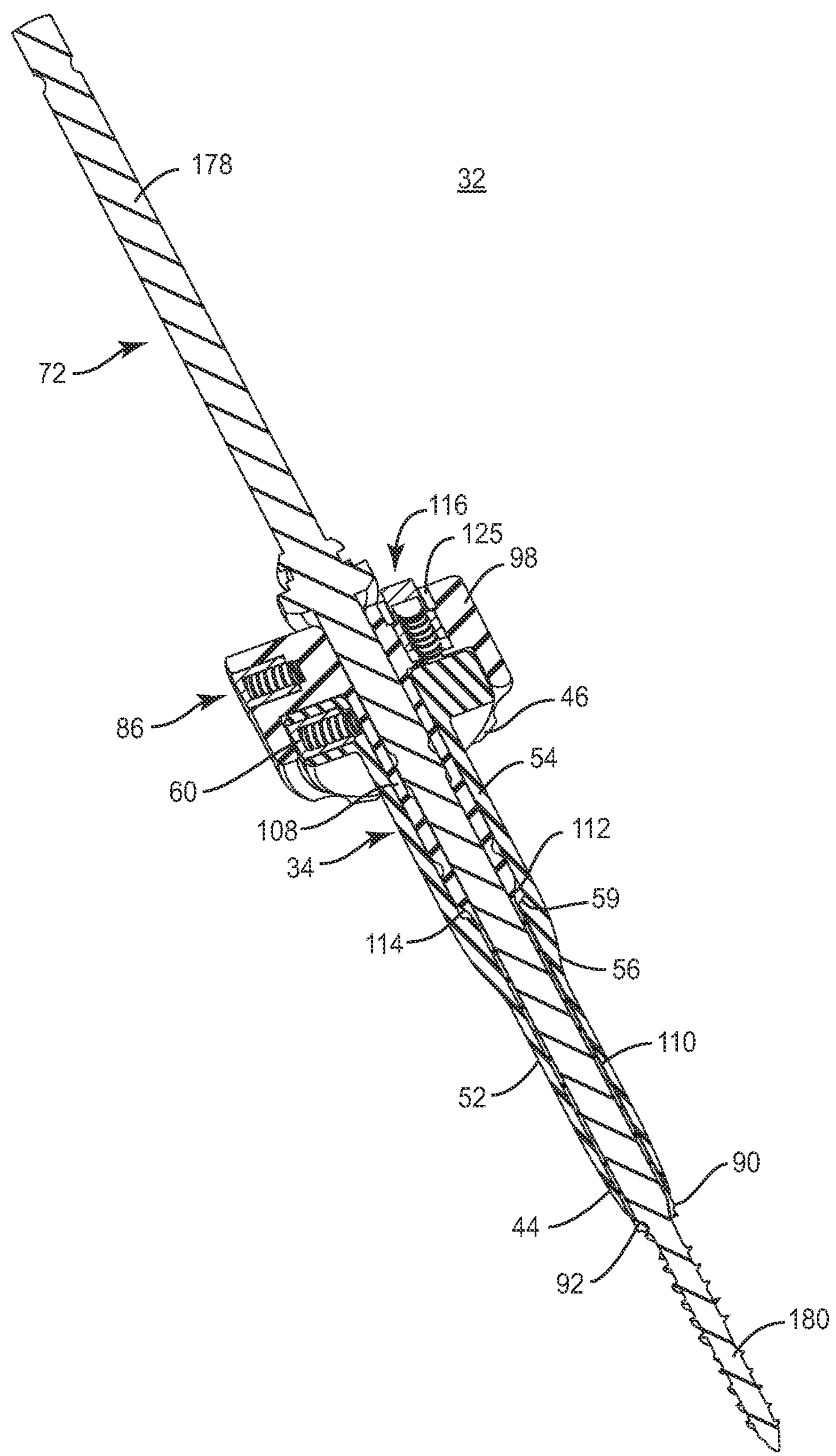
FIG. 9 is a perspective view of the instrument shown in FIG. 7 shown in cross-section.

Lock 42 is slidable in a transverse orientation between a locking orientation and a non-locking orientation. When lock 42 is in the locking orientation, sleeve 50 is positioned within passageway 38 and tap 72 is positioned within passageway 76. Surface 48 is engaged with surface 104 such that end 88 is disposed in the nested configuration within sleeve 34 and surface 62 engages surface 104, as shown in FIGS. 6, 7 and 9-11, to prevent axial translation of sleeve 34, in the direction shown by arrow A. Teeth 92 extend through opening 70 such that teeth 92 are engageable with tissue adjacent opening 70, such as, for example, cortical bone. A combined length of sections 108, 110, 112 is greater than a length of passageway 38 such that end 88 extends beyond end 44 and face 90 protrudes through opening 70 such that teeth 92 are engageable with tissue adjacent opening 70 when lock 42 is in the locking orientation, as shown in FIGS. 7-9.

When lock 42 is in the non-locking orientation, surface 48 is not engaged with surface 104 such that portion 46 is spaced apart from portion 98 and surface 62 is spaced apart from surface 104, as shown in FIGS. 1-4, to permit axial translation of sleeve 34 relative to sleeve 50, in the direction shown by arrow A, and axial translation of sleeve 50 relative to sleeve 34, in the direction shown by arrow AA. As sleeve 34 translates, in the direction shown by arrow A and/or in the direction shown by arrow AA, face 90 moves within passageway 38. Sleeve 34 is a guide configured to navigate end 44 through passageway 38 and opening 70 such that end 44 can engage tissue adjacent opening 70.

Figure 11:
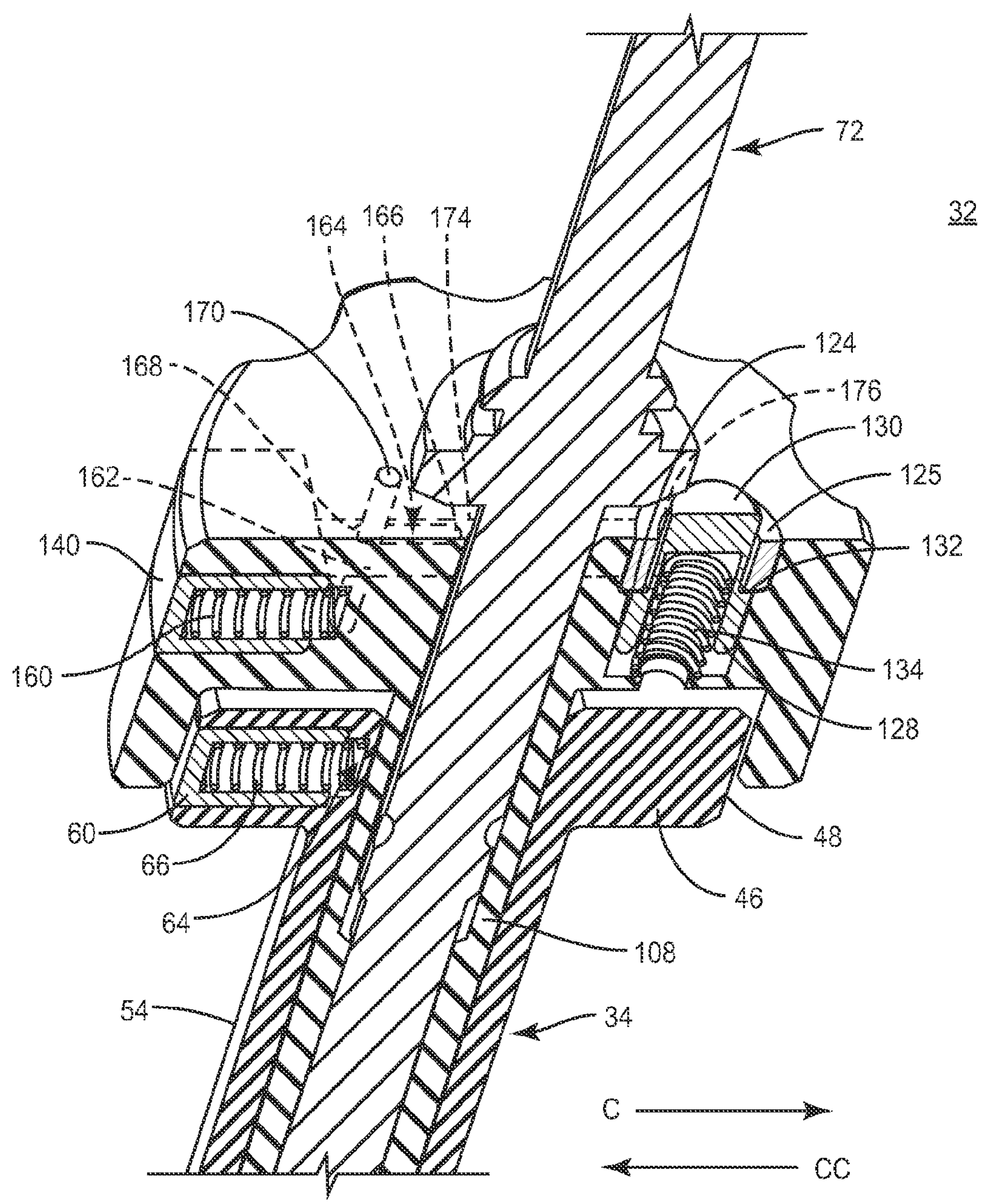
FIG. 11 is a perspective view of a portion of the instrument shown in FIG. 9 shown in cross-section, in part phantom.

Lock 86 is engageable with tap 72 between a locking orientation to prevent axial translation of tap 72 relative to sleeve 50 and a non-locking orientation such that tap 72 is axially translatable relative to sleeve 50 and end 180 is configured to penetrate tissue adjacent opening 70 and/or opening 96, such as, for example, cortical bone, and form a threaded cavity therein. When lock 86 is in the locking orientation, tab 140 is inserted into cavity 138, in the direction shown by arrow CC, such that pins 170 are positioned adjacent ends 166 and sections 190 engage groove 186, as shown in FIG. 11, to prevent axial translation of tap 72 in passageway 76 in the direction shown by arrow A or the direction shown by arrow AA. When lock 86 is in the locking orientation, tap 182 is positioned within passageway 38 and/or passageway 76 such that sleeve 34 and/or sleeve 50 prevent tap 182 from engaging tissue. When sections 190 engage groove 186, the projections of sections 192 are disposed in the grooves in the outer surface of tab 126, as shown in FIG. 12, to fix lock 86 in the locking orientation and sleeve 34 prevents end 88 from projecting through opening 70 to engage tissue.

To move lock 86 from the locking orientation to the non-locking orientation, tab 126 is translated within channel 118 until the projections of sections 192 disengage the grooves in the outer surface of tab 126 to allow arms 162 to translate within conduits 148, in the direction shown by arrow C or the direction shown by arrow CC. Tab 140 is inserted into portion 98, in the direction shown by arrow CC such that pins 170 are positioned adjacent ends 166 and tap 72 extends through an opening between portions 174 such that tap 72 can translate axially within passageway 76 in the direction shown by arrow A and the direction shown by arrow AA for selective positioning of tap 182 relative to end 44 and/or end 88. Portions 176 are positioned adjacent tab 126. Portions 176 define an opening therebetween configured to engage part 130 to prevent arms 162 from moving within conduits 148, in the direction shown by arrow C or the direction shown by arrow CC, to maintain lock 86 in the non-locking orientation. This configuration allows end 180 to project through opening 70 and opening 94, as shown in FIG. 5.

To move lock 86 from the non-locking orientation to the locking orientation, tab 126 is translated axially within channel 118, in the direction shown by arrow A, and tab 140 is simultaneously translated, in the direction shown by arrow CC, until the projections of sections 192 engage the grooves in the outer surface of tab 126 and sections 190 engage groove 186 to prevent axial translation of tap 72 in passageway 76, in the direction shown by arrow A or the direction shown by arrow AA.

In assembly, operation and use, a surgical implant system, similar to system 30 described herein, is employed with a surgical procedure for treatment of a spinal disorder affecting a section of a spine of a patient, as discussed herein. For example, system 30 can be used with a surgical procedure for treatment of a condition or injury of an affected section of the spine including vertebrae (not shown). It is contemplated that one or all of the components of system 30 can be delivered or implanted as a pre-assembled device or can be assembled in situ. System 30 may be completely or partially revised, removed or replaced.

For example, system 30 can be employed with a surgical treatment of an applicable condition or injury of an affected section of a spinal column and adjacent areas within a body, such as, for example, vertebrae. It is envisioned that system 30 may be employed with one or a plurality of vertebra. To treat a selected section of the vertebrae, a medical practitioner obtains access to a surgical site including the vertebrae in any appropriate manner, such as through incision and retraction of tissues. It is envisioned that system 30 can be used in any existing surgical method or technique including open surgery, mini-open surgery, minimally invasive surgery and percutaneous surgical implantation, whereby the vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of components of system 30 adjacent an area within the patient's body, such as, for example, the spine. Instrument 32 is delivered through the passageway adjacent surgical site within the patient's body. Lock 42 is disposed in the locking orientation or the non-locking orientation and lock 86 is disposed in the locking orientation.

In one embodiment, sleeve 34 is percutaneously navigated through the incision to and from the surgical site including the spine to avoid undesired tearing of soft tissue. This configuration facilitates percutaneous docking of sleeve 50 with tissue, such as, for example, cortical bone, while sleeve 34 supports sleeve 50 during delivery of instrument 32 to the surgical site. In one embodiment, instrument 32 includes safety features, as described herein, which prevent deployment of sleeve 50 and/or tap 72 from sleeve 34 until sleeve 34 has navigated to the surgical site to resist or prevent inadvertent or accidental exposure of the sharp tap 72 and/or toothed sleeve 50.

In one embodiment, sleeve 34 is made from a radiolucent material to facilitate visualization of instrument 32 for accurate and selective placement during navigation to the surgical site to avoid undesirable damage of soft tissue.

When instrument 32 is delivered adjacent the area within the patient's body and lock 42 is disposed in the non-locking orientation, sleeve 50 is positioned within passageway 38 and tap 72 is positioned within passageway 76, as shown in FIG. 3. Lock 42 is moved from the non-locking orientation to the locking orientation by moving sleeve 34 and sleeve 50 toward one another such that surface 48 engages surface 104 and surface 62 engages surface 104 to prevent axial translation of sleeve 50 relative to sleeve 34, in the direction shown by arrow A, and/or axial translation of sleeve 34 relative to sleeve 50, in the direction shown by arrow AA.

When lock 42 is in the locking orientation, relative movement of sleeve 50 is prevented and end 88 extends through opening 70 such that teeth 92 are engageable with tissue adjacent opening 70, such as, for example, cortical and/or cancellous bone of the spine. A medical practitioner rotates sleeve 50, in the direction shown by arrow B and/or the arrow shown by arrow B, by rotating portion 98, which causes end 88 to rotate, in the direction shown by arrow B and/or the arrow shown by arrow BB, such that teeth 92 scrape and/or cut the tissue to fix instrument 32 in position relative to the tissue in preparation for tap 72. In one embodiment, teeth 92 are configured to form a cavity in tissue configured to engage threads of an implant, such as, for example, a bone fastener.

Lock 86 is moved from the locking orientation to the non-locking orientation to allow tap 72 to translate relative to sleeve 50 so that tap 182 can move from its position within passageway 38 and/or passageway 76 and through openings 70, 96 such that tap 182 can penetrate tissue to form a cavity therein. Tap 72 is translated axially through passageway 76 and/or passageway 38, in the direction shown by arrow A, until at least a portion of tap 182 projects through opening 70 and opening 96 and is engageable with the tissue. Tap 182 is rotated by rotating portion 188, in the direction shown by arrow B and/or the direction shown by arrow BB, which causes tap 182 to penetrate the tissue and form a cavity therein. It is envisioned that an actuator can engage portion 188 to rotate tap 72, in the direction shown by arrow B and/or the direction shown by arrow BB.

After the cavity is formed within the tissue, instrument 32 may be removed from the patient's body so that an implant, such as, for example, a bone screw can be threaded into the surface of the body cavity. Prior to removal of instrument 32 from the patient's body, teeth 92 and tap 182 are withdrawn within passageway 38 and/or passageway 76, without extending through opening 70, as shown in FIGS. 1-3 and 5, to prevent teeth 92 and tap 182 from undesirably damaging tissue during removal of instrument 32. Accordingly, lock 42 is moved from the locking orientation to the non-locking orientation by inserting tab 60 into channel 58, in the direction shown by arrow C. As tab 60 is inserted into channel 58, sleeve 50 is axially translatable relative to sleeve 34, in the direction shown by arrow AA to allow surfaces 48, 104 to disengage. Once surfaces 48, 104 disengage, sleeve 50 is translated axially, in the direction shown by arrow AA, and/or sleeve 34 is translated axially, in the direction shown by arrow A, such that portion 46 is spaced apart from portion 98 and face 90 is positioned within passageway 38, without extending through opening 70. Sleeve 50 is further translated axially, in the direction shown by arrow AA, and/or sleeve 34 is further translated axially, in the direction shown by arrow A, such that tap 182 is positioned within passageway 76 and/or passageway 38, without extending through opening 70. Instrument 32 may be removed from the patient's body.

It is envisioned that tap 72 may translated axially within passageway 76, in the direction shown by arrow AA, prior to removal of instrument 32 from the patient's body such that tap 182 does not extend through opening 96. It is further envisioned that tap 72 may be removed from instrument 32 prior to removal of instrument 32 from the patient's body by translating tap 72 axially, in the direction shown by arrow AA.

In one embodiment, tap 182 is fixed within passageway 76 and/or passageway 38 during removal of instrument 32 from the patient's body to prevent tap 182 from translating axially, in the direction shown by arrow A, and prevent injury to the patient. To fix tap 182 within passageway 76 and/or passageway 38, lock 86 is moved from the non-locking orientation to the locking orientation by inserting tab 126 into channel 118, in the direction shown by arrow A, and moving tab 140, in the direction shown by arrow C, such that the projections of sections 192 are disposed within the grooves in the outer surface of tab 126. As tab 140 moves, in the direction shown by arrow C, pins 170 are positioned adjacent ends 168 and sections 190 engage groove 186, as shown in FIG. 12, such that axial translation of tap 72 is prevented, in the direction shown by arrow A and/or arrow AA, during removal of instrument 32 from the patient's body.

Following removal of instrument 32 from the patient's body, a fastener, such as for example, a bone screw having an external thread configured to engage the surface of the body cavity may be threaded into the body cavity, according to the particular requirements of the surgical treatment.

Figure 6:
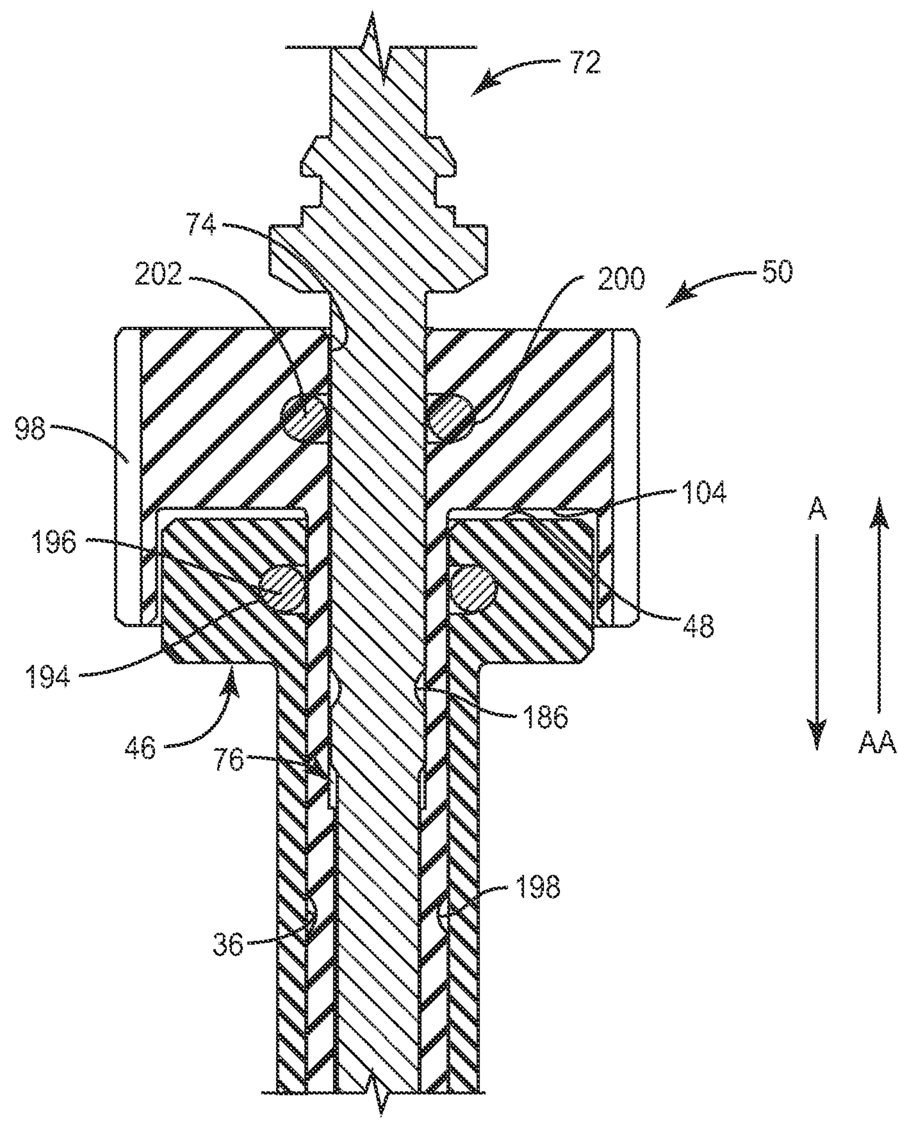
FIG. 6 is a top view of a portion of the instrument shown in FIG. 1 shown in cross-section.

In one embodiment, surface 36 includes a concave circumferential recess 194 having a material 196, such as, for example, an O-ring disposed therein. Material 196 has a circular cross-sectional configuration and a width that is greater than a depth of recess 194 such that material 196 protrudes from recess 194 into passageway 38. Material 196 is configured for disposal in a concave cavity 198 in sleeve 50 positioned between section 108 and section 112 to maintain sleeve 34 and sleeve 50 in a spaced apart relationship, as shown in FIGS. 4 and 6. It is envisioned that material 196 may be made from a deformable and/or resilient material to facilitate insertion and removal of material 196 in and out of cavity 198 and/or to maintain material 196 in cavity 198. It is contemplated that forming material 196 from a deformable and/or resilient material will also allow material 196 to engage an outer surface of section 108 when lock 42 is in the locking configuration to maintain the engagement between surface 48 and surface 104, as shown in FIG. 6. It is further envisioned that recess 194 may be variously configured and dimensioned, such as, for example, planar, concave, convex, polygonal, irregular, uniform, non-uniform, staggered, tapered, consistent or variable, depending on the requirements of a particular application. It is contemplated that material 196 may have alternate cross section configurations, such as, for example, oval, oblong triangular, square, polygonal, irregular, uniform, non-uniform, offset, staggered, and/or tapered, depending upon the requirements of a particular application.

In one embodiment, surface 74 includes a concave circumferential recess 200 having a material 202, such as, for example, an O-ring disposed therein. Material 202 has a circular cross-sectional configuration and a width that is greater than a depth of recess 200 such that material 202 protrudes from recess 200 into passageway 76. Material 202 is configured for disposal in groove 186, as shown in FIG. 4, to prevent tap 72 from translating, in the direction shown by arrow A or the direction shown by arrow AA, within passageway 76. It is envisioned that material 202 may be made from a deformable and/or resilient material to facilitate insertion and removal of material 202 in and out of groove 186 and/or to maintain material 202 in groove 186. It is contemplated that forming material 202 from a deformable and/or resilient material will also allow material 202 to engage an outer surface of tap 72, as shown in FIG. 6, to prevent axial translation of tap 72 within passageway 76, in the direction shown by arrow A and the direction shown by arrow AA. It is further envisioned that recess 194 may be variously configured and dimensioned, such as, for example, planar, concave, convex, polygonal, irregular, uniform, non-uniform, staggered, tapered, consistent or variable, depending on the requirements of a particular application. It is contemplated that material 196 may have alternate cross section configurations, such as, for example, oval, oblong triangular, square, polygonal, irregular, uniform, non-uniform, offset, staggered, and/or tapered, depending upon the requirements of a particular application.

It is envisioned that system 30 may comprise various instruments including the configuration of the present disclosure, such as, for example, inserters, extenders, reducers, spreaders, distractors, blades, retractors, clamps, forceps, elevators and drills, which may be alternately sized and dimensioned, and arranged as a kit, according to the requirements of a particular application.

The components of system 30 can be made of radiolucent materials such as polymers. Radiomarkers may be included for identification under x-ray, fluoroscopy, CT or other imaging techniques. It is envisioned that the use of microsurgical and image guided technologies may be employed to access, view and repair spinal deterioration or damage, with the aid of system 30.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:

a first member including an inner surface defining a first passageway and a first lock;

a second member disposable within the first passageway and movable relative to the first member, the second member comprising an inner surface defining a second passageway and extending between a first end comprising a second lock and a second end configured to engage tissue; and a third member disposable within the second passageway and movable relative to the second member, the third member extending between a first end and a second end configured to penetrate tissue and form a cavity therein, the second member includes a third lock engageable with the second lock to fix the second lock in a locking orientation to prevent the relative movement of the third member, wherein the first lock is engageable with the second member to prevent relative movement of the second member and the second lock is engageable with the third member to prevent relative movement of the third member.

2. A surgical instrument as recited in claim 1, wherein the members are disposable in a configuration such that the first member prevents the second end of the second member or the second end of the third member from engaging tissue.

3. A surgical instrument as recited in claim 1, wherein the members are disposable in a configuration such that the second end of the second member or the second end of the third member are extendable beyond the first member to engage tissue.

4. A surgical instrument as recited in claim 1, wherein the first member includes a protective sleeve disposed about the second end of the second member or the second end of the third member.

5. A surgical instrument as recited in claim 1, wherein the first member includes a guide configured to navigate the second end of the second member or the second end of the third member to adjacent a surgical site.

6. A surgical instrument as recited in claim 1, wherein the first lock is disposable between a locking orientation to prevent the relative movement of the second member and a non-locking orientation such that the second member is axially translatable relative to the first member.

7. A surgical instrument as recited in claim 1, wherein the first lock is resiliently biased to a locking orientation to prevent the relative movement of the second member.

8. A surgical instrument as recited in claim 1, wherein the second lock is disposable between a locking orientation to prevent the relative movement of the third member and a non-locking orientation such that the third member is axially translatable relative to the second member.

9. A surgical instrument as recited in claim 1, wherein the second lock is resiliently biased to a locking orientation to prevent the relative movement of the third member.

10. A surgical instrument as recited in claim 9, wherein the third lock is resiliently biased to a non-locking orientation.

11. A surgical instrument as recited in claim 1, wherein the second end of the second member includes a distal face having at least one penetrating element engageable with tissue.

12. A surgical instrument as recited in claim 1, wherein the second end of the second member includes a plurality of teeth.

13. A surgical instrument as recited in claim 1, wherein the second end of the third member includes a screw tap configured to penetrate tissue and form the cavity.

14. A surgical instrument as recited in claim 1, wherein the second end of the second member is disposed in a nested configuration with the first member.

15. A surgical instrument comprising:

an outer sleeve including an inner surface defining a passageway and extending between a first end comprising a first lock and a second end configured for disposal adjacent a surgical site;

an inner sleeve disposable within the passageway of the outer sleeve, the inner sleeve comprising an inner surface defining a passageway and extending between a first end comprising a second lock and a second end; and a tap disposable within the passageway of the inner sleeve, the tap extending between a first end and a second end, wherein the first lock is engageable with the inner sleeve between a locking orientation in which axial translation of the inner sleeve relative to the outer sleeve is prevented and the second end of the inner sleeve is engageable with cortical bone and a non-locking orientation such that the inner sleeve is axially translatable relative to the outer sleeve, and the second lock is engageable with the tap between a locking orientation to prevent axial translation of the tap relative to the inner sleeve and a non-locking orientation such that the tap is axially translatable relative to the inner sleeve and the second end of the tap is configured to penetrate the cortical bone and form a cavity therein.

16. A surgical instrument as recited in claim 15, wherein the outer sleeve defines a longitudinal axis and the first lock is slidable in a transverse orientation between the locking orientation and the non-locking orientation.

17. A surgical instrument as recited in claim 15, wherein the inner sleeve includes a third lock engageable with the second lock to fix the second lock in a locking orientation to prevent the relative movement of the tap.

18. A surgical instrument as recited in claim 15, wherein the second end of the inner sleeve is disposed in a nested configuration with the outer sleeve.

19. A surgical instrument comprising:

an outer sleeve defining a longitudinal axis and including an inner surface defining a passageway, the outer sleeve extending between a first end comprising a first transverse lock biased to a locking orientation and a second end configured for disposal adjacent a surgical site;

an inner sleeve disposable within the passageway of the outer sleeve, the inner sleeve comprising an inner surface defining a passageway and extending between a first end comprising a second transverse lock biased to a locking orientation and a second end including a distal face having a plurality of teeth; and a tap disposable within the passageway of the inner sleeve, the tap extending between a first end and a second end, wherein the first lock is engageable with the inner sleeve between the locking orientation in which axial translation of the inner sleeve relative to the outer sleeve is prevented and the teeth are engageable with cortical bone and a non-locking orientation such that the inner sleeve is axially translatable relative to the outer sleeve, and the second lock is engageable with the tap between the locking orientation to prevent axial translation of the tap relative to the inner sleeve and a non-locking orientation such that the tap is axially translatable relative to the inner sleeve and the second end of the tap is configured to penetrate the cortical bone and form a cavity therein.

* * * * *

UNITED STATES PATENT AND TRADEMARK OFFICE

CERTIFICATE OF CORRECTION

PATENT NO. : 9,198,674 B2
APPLICATION NO. : 13/715494
DATED : December 1, 2015
INVENTOR(S) : Benson et al.

It is certified that error appears in the above-identified patent and that said Letters Patent is hereby corrected as shown below:

IN THE SPECIFICATION

In Column 5, Line 43, delete "sleeve 32" and insert -- sleeve 34 --, therefor.

IN THE CLAIMS

In Column 15, Line 41, in Claim 10, delete "as recited in claim 9," and insert -- as recited in claim 1, --, therefor.

Signed and Sealed this
Twenty-sixth Day of April, 2016

Michelle K. Lee
*Director of the United States Patent and Trademark Office*